United States Patent [19]
Chaudiere et al.

[11] Patent Number: 5,861,262
[45] Date of Patent: Jan. 19, 1999

[54] METHOD OF THE SPECIFIC IMMUNOASSAY OF HUMAN PLASMA GLUTATHIONE PEROXIDASE, KIT FOR ITS IMPLEMENTATION, OLIGOPEPTIDES AND ANTIBODIES SPECIFIC FOR THE METHOD

[75] Inventors: Jean Chaudiere, Saint Maur; Arnaud Lemainque, Combs-la-Ville; Patricia Malette, Saint Maur, all of France

[73] Assignee: OXIS Isle of Man, Limited, Portland, Oreg.

[21] Appl. No.: 428,188

[22] PCT Filed: Sep. 1, 1994

[86] PCT No.: PCT/FR94/01031

§ 371 Date: May 2, 1995

§ 102(e) Date: May 2, 1995

[87] PCT Pub. No.: WO95/06719

PCT Pub. Date: Mar. 9, 1995

[30] Foreign Application Priority Data

Sep. 3, 1993 [FR] France .................................. 93 10504

[51] Int. Cl.[6] .................................................. G01N 33/573
[52] U.S. Cl. ........................... 435/7.4; 435/961; 435/975; 436/518; 436/543; 436/547; 436/808; 530/327; 530/387.9; 530/402; 530/403; 530/806; 530/810
[58] Field of Search ............................. 435/7.4, 961, 975; 436/518, 543, 547, 808; 530/395, 402, 403, 806, 810, 327, 387.9

[56] References Cited

U.S. PATENT DOCUMENTS

5,089,408 2/1992 Akasaka et al. .
5,187,078 2/1993 Ohya et al. .

FOREIGN PATENT DOCUMENTS

0392369 10/1990 European Pat. Off. ................. 435/13

OTHER PUBLICATIONS

Harlow, E. and D. Lane, Antibodies, Cold Spring Harbor Laboratory, pp. 86–87, 1988.
Avissar, N. et al., Blood, vol. 73, No. 1, pp. 318–323, Jan. 1989.
Yoshimura, S. et al., J. Biochem., vol. 109, pp. 918–923, 1991.

Chu et al., "Expression of Plasma Glutathione Peroxidase in Human Liver . . . " Blood, vol. 79, No. 12, pp. 3233–3238, Jun. 15, 1992.

Yoshimura et al., "The human plasma glutathione peroxidase—encoding gene . . . ," Gene, vol. 145, 293–297, 1994.

Esworthy et al., "Characterization and Partial Amino Acid Sequence of Human Plasma Glutathione Peroxidase," Arch. Biochem. Biophys. 286(2):330–336, 1991.

Journal of Biochemistry., vol. 108, 1990, Tokyo JP pp. 145–148 K. Takahashi et al. Primary structure of human plasma glutathion peroxidase deduced from cDNA sequences'.

Proceedings of The National Academy of Sciences of USA., vol. 81 Jul. 1984, pp. 3998–4002; H.M. Geystn et al. Use of peptide synthesis to probe viral antigens for epitopes to a resolution of a single amino acid'.

Proceedings of The National Academy of Sciences of USA., vol. 82, Jan. 1985, Washington US pp. 178–182; H.M. Geysten et al. "Small peptides induce antibodies with a sequence and structural requirement for binding antigen comparable to antibodies raised against the native protein".

*Primary Examiner*—Carol A. Spiegel
*Attorney, Agent, or Firm*—Jacobson, Price, Holman & Stern, PLLC

[57] ABSTRACT

An oligopeptide having an amino acid sequence
 Glu Pro Gly Asn Ser Glu Ile Leu Pro Thr Leu Lys
and variants thereof; immunogenic conjugates obtained therefrom; antibodies produced by means of said conjugates and which specifically recognize human plasma glutathione peroxidase (pl.GPx); methods for assaying human plasma glutathione peroxidase (pl.GPx); and assaying kits. The invention is useful in the medical diagnosis, treatment and monitoring of pathologic conditions induced by a variation in pl.GPx, for example, hepatic tumors, acute rejection of renal or hepatic graft, renal insufficiency and selenium deficiency.

32 Claims, 1 Drawing Sheet

Figure 1

| | | | | | | | | | | | | | | |
|---|---|---|---|---|---|---|---|---|---|---|---|---|---|---|
|Met|Ala|Arg|Leu|Leu|Gln|Ala|Ser|Cys|Leu|Leu|Ser|Leu|Leu|Leu|Ala|

```
Met Ala Arg Leu Leu Gln Ala Ser Cys Leu Leu Ser Leu Leu Leu Ala
1                 5                 10                    15

Gly Phe Val Ser Gln Ser Arg Gly Gln Glu Lys Ser Lys Met Asp Cys
                20                  25              30

His Gly Gly Ile Ser Gly Thr Ile Tyr Glu Tyr Gly Ala Leu Thr Ile
            35              40              45

Asp Gly Glu Glu Tyr Ile Pro Phe Lys Gln Tyr Ala Gly Lys Tyr Val
    50                  55              60

Leu Phe Val Asn Val Ala Ser Tyr Xaa Gly Leu Thr Gly Gln Tyr Ile
65              70                  75                      80

Glu Leu Asn Ala Leu Gln Glu Glu Leu Ala Pro Phe Gly Leu Val Ile
                85              90              95

Leu Gly Phe Pro Cys Asn Gln Phe Gly Lys Gln Glu Pro Gly Glu Asn
            100             105             110

Ser Glu Ile Leu Pro Thr Leu Lys Tyr Val Arg Pro Gly Gly Gly Phe
        115             120             125

Val Pro Asn Phe Gln Leu Phe Glu Lys Gly Asp Val Asn Gly Glu Lys
    130             135             140

Glu Gln Lys Phe Tyr Thr Phe Leu Lys Asn Ser Cys Pro Pro Thr Ser
145             150             155             160

Glu Leu Leu Gly Thr Ser Asp Arg Leu Phe Trp Glu Pro Met Lys Val
            165             170             175

His Asp Ile Arg Trp Asn Phe Glu Lys Phe Leu Val Gly Pro Asp Gly
            180             185             190

Ile Pro Ile Met Arg Trp His His Arg Thr Thr Val Ser Asn Val Lys
            195             200             205

Met Asp Ile Leu Ser Tyr Met Arg Arg Gln Ala Ala Leu Gly Val Lys
    210             215             220

Arg Lys
225
```

METHOD OF THE SPECIFIC IMMUNOASSAY OF HUMAN PLASMA GLUTATHIONE PEROXIDASE, KIT FOR ITS IMPLEMENTATION, OLIGOPEPTIDES AND ANTIBODIES SPECIFIC FOR THE METHOD

The present invention relates to a method for assaying human plasma glutathione peroxidase (pl.GPx) and a ready-for-use kit for the implementation of the said method; it is based on the selection of peptide sequences of pl.GPx and the in vitro synthesis of the said sequences as well as on the production and use of antibodies against the said sequences and which specifically recognize pl.GPx.

BACKGROUND OF THE INVENTION

Three types of human glutathione peroxidase have been characterized: plasma glutathione peroxidase (pl.GPx), intracellular glutathione peroxidase (c.GPx) which is essentially active on hydrophilic substrates, and glutathione peroxidase which is active on phospholipid hydroperoxides as well as on other lipid substrates (PHGPx). These enzymes catalyse the reduction of hydroperoxides ($H_2O_2$ or ROOH) by glutathione (GSH). These enzymes are selenoproteins which contain a selenocysteine within their active site. c.GPx and pl.GPx are homotetramers whereas PHGPx is exclusively monomeric Biochem. Biophys. Acta, 839, 62–70 (1985).

Originally purified from plasma J. Biol. Chem., 262, No.36, 17398–17403 (1987); Arch. Biochem. Biophys., 256,No.2, 677–686 (1987), pl.GPx represents 0.007% of the total plasma protein mass. pl.GPx has also been isolated from human maternal milk J. Nutr., 121, No.8, 1243–1249 (1991).

Of glycoprotein nature, pl.GPx exists in the form of a homotetramer of a molecular weight of 94 kDa J. Biol. Chem., 262, No.36, 17398–17403 (1987). Each subunit, characterized by a molecular weight of 21.5 to 23 kDa J. Biol. Chem., 262, No.36, 17398–17403 (1987); J. Biochem., 108, 145–148 (1990), contains a selenocysteine in its active site.

Recently, a study performed in rats has shown that pl.GPx is predominantly synthesized by the renal cell (Yoshimura et al. J. Biochem. 109; (1991); 918–923) whereas another study has shown that a tumorous hepatic cell line (Hep G2) of human origin is capable of synthesizing this pl.GPx (AVISSAR et al. J. Biol. Chem. 264; 1989; 15850–15855).

Given the low concentrations of plasma glutathione, the principal role of pl.GPx remains uncertain. The specific activity of pl.GPx is about ten times lower than that of c.GPx Arch. Biochem. Biophys., 256, No.2, 677–686 (1987).

The primary sequence of human pl.GPx was determined from the cDNA and published by Takahashi et al. J. Biochem., 108; (1990); 145–148. It was not possible to completely sequence the pl.GPx and to identify the N-terminal end because of the glycosylation affecting this end. The exact number of residues per subunit therefore remains unknown.

pl.GPx differs considerably from c.GPx from the structural point of view:. absence of glycosylation and intramolecular disulphide bridges for the cellular form Arch. Biochem. Biophys., 256, 677–686 (1987); Blood, 73, 318–323 (1989), weak sequence homology between the two enzymes (of the order of 44% Nucleic Acids Res., 15; (1987); 5484; Nucleic Acids Res., 15; (1987); 7178).

Measurement of the pl.GPx level in plasma is a good indicator of a possible state of selenium deficiency in the body. Within the framework of experiments designed to quantify the influence of a deficiency and then of a supply of selenium in man, it has been shown that the average glutathione peroxidase levels do not vary at the same rate depending on whether the plasma form or the cellular form is involved. Thus, the pl.GPx level in plasma begins to increase from the early days of treatment to reach a normal value after two to four weeks. The time necessary for the value of the normal level of c.GPx to be reestablished is longer: three to four months Amer. J. Clin. Nutr., 41; (1985); 735–747.

Furthermore, and following the studies previously carried out in rats, a number of renal pathologies could be detected by the measurement of pl.GPx.

None of the known methods of assaying enzymatic activity currently permit the specific assay of pl.GPx in biological fluids or in tissue extracts.

The most commonly used method of assaying glutathione peroxidase activity involves an enzymatic coupling calling into play the regeneration of reduced glutathione by the glutathione reductase present in excess; this reaction is accompanied by the oxidation of a reduced cofactor, NADPH, whose rate of disappearance can be easily monitored as a function of time. Under these conditions, the kinetics of oxidation of NADPH corresponds to the kinetics of oxidation of glutathione and, consequently, to the kinetics of reduction of hydroperoxide. However, no hydroperoxide substrate specific for pl.GPx or c.GPx exists.

Discrimination between the activity of c.GPx and the activity of pl.GPx is therefore impossible at the present time.

Given the fact that the specific activity of c.GPx is approximately ten times greater than that of pl.GPx, a contamination of 1% by mass by c.GPx will introduce an overestimation of the order of 10% of the pl.GPx activity. A slight haemolysis occurring in a blood sample can thus introduce a large error into the calculation of the pl.GPx activity of the circulating plasma or the serum.

SUMMARY OF THE PRESENT INVENTION

The objective of the present invention is therefore to develop a new method of assaying GPx which makes it possible to distinguish pl.GPx and c.GPx and, in particular, to specifically assay pl.GPx by an immunoenzymatic method. No immunological method of assaying pl.GPx has yet been developed because the high homology of primary sequence of pl.GPx and c.GPx causes cross reactions between the antibodies and the 2 types of molecules.

The present invention is also directed to oligopeptides and variants thereof, for use in an assay, immunogenic conjugates comprising said oligopeptides or vaiants thereof, antibodies raised against said conjugates of the present invention.

BRIEF DESCRIPTION OF DRAWING

FIG. 1 (SEQ. ID. NO. 1) represents the primary sequence of plasma glutathione perixidase deduced from the nucleic acid sequence of the cDNA, as published by Takahashi K., Akasada M., Yamamoto Y., Kobayashi C., Mizogunchi J. & Koyama J., (1990), J. Biochem., 108, 145–148. The amino acids, in italics are common to pl.GPx and c.GPx.

FIG. 1 is attached to the description in order to facilitate the reading, but is not necessary for implementation of the invention.

DESCRIPTION OF PREFERRED EMBODIMENTS

In order to overcome problems in the art, the Applicant evaluated the immunogenicity of various synthetic oligopeptides derived from the published sequence of the pl.GPx, selected an oligopeptide and a series of variants thereof, in order to use them in the form of immunogenic conjugates to induce, in laboratory animals, the production of antibodies specific for the chosen sequence, demonstrated that the said antibodies specifically recognize pl.GPx, developed a method for the immunoassay of pl.GPx based on its immunocapture by the said antibodies, and incorporated the said antibodies into a ready-for-use assay kit.

The published sequence (Takahashi—see above and see FIG. 1 (SEQ. ID. NO: 1:)) of pl.GPx was studied by means of a software which makes it possible to define the hydrophilicity and flexibility profile, and consequently the probability profile for exposure at the surface of the molecule, of peptide sequences. On this basis, a series of oligopeptides were chosen and synthesized, from 13 to 16 amino acids in length, having overlapping sequences so as to cover a large portion of the pl.GPx sequence. The sequence surrounding and comprising the active site was removed because of its too high homology with the corresponding c.GPx sequence.

These oligopeptides were grafted as haptens on bovine serum albumin (BSA) so as to be injected into rabbits. The serum from the rabbits was collected and the antibody titre was evaluated, in a first stage, in a homologous system, against the peptides used as immunogens, then against pl.GPx in order to select the antibodies which can be potentially used in a diagnostic test. The results were confirmed by other titrations and by competition tests in the presence of soluble antigen.

The Applicant thus selected an oligopeptide, whose sequence extends from residues Glu 108 to Lys 120 of the pl.GPx sequence as published (in Takahashi). This oligopeptide (SEQ. I.D. No. 1) constitutes the basis of the present invention.

The invention also extends to variants of this sequence in which, for technical reasons which can facilitate the synthesis of the oligopeptide or produce a more stable molecule, one or two amino acids have been replaced by an equivalent amino acid, that is to say without this replacement modifying the spatial configuration or the hydrophilic character or the immunogenicity of the entire oligopeptide.

The invention also extends to variants of this sequence, either shorter by a few amino acids, at the N-terminal or C-terminal end or both, or longer by a few amino acids (it being possible to obtain such variants by chemical synthesis or by enzymatic digestion of the naturally occurring molecule), so long as the said variants permit the induction of antibodies of the same specificity as the chosen sequence, that is to say antibodies specific for pl.GPx.

The oligopeptides thus defined are used as immunogens in the form of haptens coupled to a carrier protein of the ovalbumin or serum albumin type and the like.

The synthesis of the chosen oligopeptides was carried out by means of a solid-phase synthesizer, adding amino acids from the C-terminal end towards the N-terminal end, under conventional conditions. During the synthesis, an amino acid which is not part of the chosen sequence was added, either at the C-terminal, or at the N-terminal, in order to allow the coupling of the oligopeptide to the carrier protein.

The immunogenic conjugates thus obtained were injected into laboratory animals (mice, rats, rabbits, goats and the like) according to a conventional procedure in order to obtain antibodies at a high titre.

The present invention also relates to the antibodies whose production results from the use of the immunogenic conjugates defined above. These antibodies are purified by affinity chromatography on a SEPHAROSE® type gel grafted with the same oligopeptide which served as hapten in the immunogenic conjugate, so as to select antibodies having the desired specificity. This is controlled by the same immunoenzymatic assays which were used to choose the oligopeptide and which show that the purified antibodies specifically recognize naturally occurring pl.GPx, excluding other glutathione peroxidases.

The present invention also extends to monoclonal antibodies exhibiting the same specificity, which are induced according to conventional procedures using, as immunogen, the oligopeptide according to the present invention and which are purified according to conventional methods.

The present invention also relates to a new method of assaying pl.GPx by immunocapture by means of antibodies as defined above, which will be designated hereinbelow "anti-peptide antibodies", followed by a revealing of the "captured" pl.GPx, by a second "revealing antibody", this type of method being commonly called "sandwich immunoassay".

This method therefore comprises:

the binding of the anti-peptide antibodies to a support;

the immunocapture by the said antibodies of the pl.GPx present in a sample of biological material to be assayed;

the revealing of the immunocaptured pl.GPx by a labelled anti-natural pl.GPx antibody.

Other embodiments of the same immunocapture assay principle can also be envisaged and form part of the present invention.

According to a preferred embodiment of the method, the anti-peptide antibodies are bound to a support which may be a conventional type plate or microplate well for dilution titration, or polystyrene beads or any other material capable of binding antibodies.

The antibodies thus bound permit the specific immunocapture of the pl.GPx present in the sample to be assayed, the latter being preferably serially diluted.

The pl.GPx thus captured by the anti-peptide antibody is revealed with the aid of a second antibody which is labelled in order to increase the sensitivity of the detection. The second type of antibody or revealing antibody is obtained after immunization of animals with purified pl.GPx; these antibodies are purified by double extraction with caproic acid and then with ammonium sulphate; they are then labelled by coupling with an enzyme whose activity will be revealed in the presence of its substrate, by colorimetry (ELISA type test) or labelled with a radioactive isotope (RIA type test) or labelled with a fluorescent substance. The second type of antibody may optionally be a monoclonal antibody.

The pl.GPx titre of the sample to be assayed is determined by comparison with a reference curve established with a standard sample of purified pl.GPx.

The advantage of the method according to the present invention is its very high specificity (that is to say the recognition of plasma GPx with the exclusion of others), which is brought about by the use of the anti-peptide antibody selected for this purpose.

The present invention also relates to a ready-for-use kit or set for the implementation of the assay method described above. This kit comprises:

a titration plate, divisible or otherwise, preferably with 96 wells, in which the anti-peptide antibody has been bound, according to a conventional method, and covers the entire surface of the wells, a solution for diluting the samples to be assayed, preferably consisting of a buffered solution (Tris or phosphate), NaCl, protein (casein, ovalbumin or serum albumin and the like) at a concentration of 0.1 to 1%, detergent and preserving agent (sodium azide or merthiolate) and a washing solution of the same composition but without proteins, a standard consisting of pl.GPx purified from human plasma, and freeze-dried, a solution of labelled anti-pl.GPx revealing antibodies; these antibodies may be polyclonal or monoclonal and result from an immunization, according to a conventional procedure, with purified human pl.GPx; these antibodies are labelled either with biotin, or with a revealing enzyme (such as alkaline phosphatase or horseradish peroxidase). The antibody solution is prepared in Tris or phosphate buffer containing 150 mM NaCl, 0.1 to 1% of overload protein (serum albumin, ovalbumin or casein), glycerol and a preserving agent, a substrate for revealing the antibody labelling, such as for example pNPP (4-nitrophenylphosphate) for alkaline phosphatase, ortho-phenylenediamine for peroxidase and so on.

The kit according to the invention can be used for any assay of pl.GPx in biological fluids or tissue extracts, in particular for the diagnosis and therapeutic monitoring of renal or hepatic pathologies and of conditions relating to nutritional deficiency in selenium.

The potential applications include:

the diagnosis of conditions relating to selenium deficiency, in particular in malnourished subjects, elderly persons and patients subjected to an artificial nutrition procedure enterally or parenterally, the diagnosis or therapeutic monitoring of renal insufficiency, in particular in dialysis patients, the early diagnosis of acute rejection of hepatic or renal graft, the diagnosis of certain hepatic tumours or the monitoring of the chemotherapeutic treatments of these tumours.

The following examples illustrate specific aspects of the development of the invention as well as embodiments thereof, without however limiting its scope.

EXAMPLE 1

Synthesis and Selection of the Oligopeptides

The amino acid sequence of pl.GPx deduced from cDNA and published by Takahashi et al. (J. Biochem. 108, (1990); 145–148 see FIG. 1 (SEQ. ID. NO. 1)-) was analysed by means of a software which makes it possible to define the hydrophilicity and flexibility profile of the primary sequence.

The following oligopeptides were chosen and synthesized:

| Code No. | Length in amino acids | Sequence* C' N' | % homology with c.GPX |
|---|---|---|---|
| BXT-02-2003 | 15 | Lys 27 to Tyr 41 | 13 |
| BXT-02-2005 | 15 | Ser 37 to Glu 51 | 27 |
| BXT-02-2007 | 16 | Thr 47 to Gly 61 + Cys | 25 |
| BXT-02-2009 | 13 | Phe 56 to Val 67 + Cys | 31 |
| BXT-02-2011 | 15 | Tyr 79 to Gly 93 | 47 |
| BXT-02-2013 | 16 | Phe 99 to Ser 113 + Tyr | 69 |
| BXT-02-2015 | 14 | Glu 108 to Tyr 121 | 57 |
| BXT-02-2017 | 14 | Lys 120 to Gln 133 | 86 |
| BXT-02-2019 | 16 | Val 129 to Gly 143 + Tyr | 75 |
| BXT-02-2021 | 16 | Asp 139 to Lys 153 + Cys | 44 |
| BXT-02-2023 | 15 | Tyr 149 to Leu 163 | 33 |
| BXT-02-2025 | 15 | Thr 159 to Pro 173 | 20 |
| BXT-02-2027 | 16 | Tyr + Leu 169 to Phe 183 | 37 |
| BXT-02-2029 | 16 | Tyr + Ile 179 to Ile 193 | 81 |
| BXT-02-2031 | 15 | Gly 189 to Thr 203 | 47 |
| BXT-02-2033 | 16 | His 199 to Tyr 214 | 19 |
| BXT-02-2001 | 13 | Tyr 214 to Lys 226 | 8 |
| pl.GPx | 226 | | 44 |

*The numbering corresponds to that of the published sequence; (SEQ ID NO.1) an amino acid was sometimes added (+) in order to facilitate the coupling to the carrier protein.

The oligopeptides were prepared under the following conditions:

a) Synthesis

The overall conditions for synthesis are extracted from published procedures (Synthetic polypeptides as antigens, M. H. V. VAN REGENMORTEL, J. P. BRIAND, S. MULLER & S. PLAUE, 1988), Ed. R. H. Burdon and P. H. Van Knippenberg-Elsevier. The sequences are synthesized on a solid phase in the direction "C-terminal end" towards the "N-terminal end".

The purity of the amino acids used for the syntheses is always greater than or equal to 99% (HPLC purity).

The different reagents and solvents involved in the cutting step (hydrofluoric acid, ether, p-cresol and trifluoroacetic acid) are characterized by a purity of at least 99%.

After precipitation and filtration by means of ether, the peptide is solubilized in trifluoroacetic acid (TFA), the solvent evaporated and the peptide reprecipitated with ether.

b) Purification

The purification of the peptides is performed by MPLC* at a flow rate of, depending on the case, between 10 and 200 ml/min. The preparative column used contains a reverse phase ($C_{18}$ column). The separation is obtained by means of a gradient (25 to 60% TFA) programmed over 30 minutes.

The fractions derived from this purification are analysed by HPLC* on a $C_{18}$ column and only the fractions having a required purity are freeze-dried.

*MPLC=medium-pressure liquid chromatography

*HPLC=high-pressure liquid chromatography.

c) HPLC Analysis

The analysis is performed on a $C_{18}$ column. A gradient (10 to 60% triethylamine phosphate-TEAP-) is programmed over 15 minutes and the detection is carried out by a UV spectrophotometric detector.

d) Preparation of the Conjugate

The oligopeptides are coupled to a carrier protein so as to be used within the framework of a programme of immunizations of animals.

The conjugate necessarily consists of:

*a hapten represented by one of the oligopeptide secuences described above onto which there has generally been grafted, either at the N-, or C-terminal end, any amino acid (such as for example tyrosine). The additional residue is always incorporated into the polypeptide chain during the peptide synthesis. This additional amino acid serves as a linkage between the sequence itself and a bifunctional reagent (such as bisdiazobenzidine, glutaraldehyde, m-maleimidobenzoyl-N-hydroxysuccinimide ester, carbodiimide) which is used to couple the polypeptide structure to a carrier protein.

*a carrier protein such as ovalbumin or OVA, bovine serum albumin or BSA, keyhole limpet hemocyanin (or KLH).

coupling of an oligopeptide and bovine serum albumin by bisdiazobenzidine (BDB):

The use of this coupling agent is particularly recommended in the case where the residue situated at the N- or C-terminal end is a tyrosine. Before coupling to BDB, the peptide may have undergone any treatment intended to protect certain reaction sites such as for example a citraconylation performed within the framework of the protection of free $NH_2$ or SH functional groups.

The coupling is carried out according to the following procedure: Dissolve the peptide in 50 mM HEPES buffer pE 8.5 in an amount of 0.2 mg/ml. Add the citraconic acid in several portions in a molar excess of 10 relative to the reactive groups: the pH is adjusted to 8.5–9 with 1M sodium hydroxide. Incubate for 1 hour at room temperature with moderate stirring. Prepare the benzidine at a concentration of 5 mg/ml in 0.2M hydrochloric acid. Add 3.5 mg of sodium nitrite per ml of benzidine solution, allow to incubate for two hours at 4° C., with gentle stirring, before using the BDB thus prepared. All the next steps are performed at 4° C.

Carry out the coupling itself by dissolving 2.5 mg of serum albumin in 10 ml of 0.16M borate buffer pH 9 containing 0.13M NaCl and then by adding the peptide in a BSA/peptide molar ratio of the order of 1/30 to 1/40. Leave stirring for 10 minutes. Introduce into the mixture thus produced 100 μl of BDB and maintain a moderate stirring for two hours. Regularly adjust the pH to 9 by adding 1M sodium hydroxide. Dialyse the solution in order to remove the excess reagent and peptide against a PBS buffer solution or physiological solution. If necessary, carry out beforehand the step of deprotecting the citraconic acid-treated residues by dialysing the solution with a 5% acetic acid solution.

The bovine serum albumin-bound oligopeptides were used to immunize rabbits, according to a conventional procedure:

A mass of conjugate corresponding to 100 μg of peptide is used per injection. The injection is performed intradermally and repeated 3 times at 3 to 4 week intervals. The serum is collected and the response with respect to antibodies directed against the oligopeptide ("anti-peptide antibodies") is measured (by a test which will be described in Example 4).

In order to choose the immunogenic peptide, it is necessary to measure both the anti-peptide antibody and the anti-natural pl.GPx antibody titre and to verify that the anti-pl.GPx antibodies (induced in rabbits) recognize the peptide. The results of these tests appear in the following table.

| serum evaluated: Code no. for the peptides | Material used to sensitize the microplates: | | |
|---|---|---|---|
| | peptides anti-peptide | pl.GPx anti-peptide Titers | peptides anti-pl.GPx |
| BXT-02-2003 | 1/2,000 | 1/1,000 | 1/100 |
| BXT-02-2005 | 0 | 0 | 0 |
| BXT-02-2007 | 1/3,000 | 1/1,000 | 0 |
| BXT-02-2009 | 0 | 0 | 0 |
| BXT-02-2011 | 1/10,000 | 1/1,000 | 1/300 |
| BXT-02-2013 | 1/3,000 | <1/1000 | 0 |
| BXT-02-2015 | 1/5,000 | 1/2,000 | 1/1,400 |
| BXT-02-2017 | 1/1,000 | 0 | 0 |
| BXT-02-2019 | 1/5,000 | 1/2,000 | 0 |
| BXT-02-2021 | 1/9,000 | 1/4,000 | 1/4,000 |
| BXT-02-2023 | 1/3,000 | 1/1,000 | 1/100 |
| BXT-02-2025 | 0 | 0 | 1/600 |
| BXT-02-2027 | 1/7,000 | 0 | 1/1,300 |
| BXT-02-2029 | 1/6,000 | 0 | 1/500 |
| BXT-02-2031 | 0 | 0 | 0 |
| BXT-02-2033 | 0 | 0 | 0 |
| BXT-02-2001 | 1/2,000 | 0 | 0 |
| natural pl.GPx | — | anti-pl.GPx 1/10,000 | — |

After this selection 4 sequences were retained and subjected to other analyses.

It was verified that the corresponding antibodies did not have an affinity for erythrocytic GPx (c.GPX)

An assay based on competition (see Example 5) between the recognition of pl.GPx insolubilized onto a microtitre plate and recognition of pl.GPx in solution, by the anti-peptide antibodies made it possible to verify whether the antibodies are capable of binding to the protein in solution.

The pl.GPx concentrations necessary to obtain about 50% inhibition are the following (the incubation times for the colorimetric revealing at 37° and the optical density or the absorbance read in the absence of inhibitor are in brackets):

| peptides | inhibition by pl.GPx in solution | |
|---|---|---|
| BXT-02-2003 | 1 μg/ml | (50 min. 0.3 O.D. u) |
| BXT-02-2015 | 5 μg/ml | (30 min. 1.4 O.D. u) |
| BXT-02-2019 | 5 μg/ml | (25 min. 0.6 O.D. u) |
| BXT-02-2021 | no inihibition | (40 min. 1.2 O.D. u) |
| pl.GPX (reference) | 0.3 to 2 μg/ml | (40 min. 1.3 O.D. u) |

By considering these results as a whole, the peptide BXT-02-2015 was chosen; its sequence is indicated below for memory:

Glu Pro Gly Glu Asn Ser Glu Ile Leu Pro Thr Leu Lys

It corresponds to residues 108 to 120 of the published sequence.

This sequence was grafted onto ovalbumin by its C-terminal end and by its N-terminal end after addition of a tyrosine residue in order to facilitate the coupling. It can be seen in the following table that the second mode of grafting induces a much higher titre.

| Peptides | Sensitization of the microplates: | |
|---|---|---|
| | peptide | p1.GPX |
| | Titre of the anti-peptide serum: | |
| Glu 108 - Lys 120 - Tyr | 1/5,000 | 1/2,099 |
| Tyr - Glu 108 - Lys 120 | 1/15,000 | 1/12,000 |

EXAMPLE 2

Production of Anti-Peptide Polyclonal Antibodies

The selected peptide, grafted onto ovalbumin, as described in the preceding example, was injected into rabbits according to the following procedure:

injection: intradermally, 1 ml per rabbit of a vol/vol mixture of 100 µg of peptide in PBS buffer and Freund adjuvant;

booster injections: under the same conditions (with incomplete Freund's adjuvant), at 3 to 4 week intervals;

collection of blood and centrifugation of the serum after one night at 4° C. or 2 hours at room temperature;

purification of the antibodies (see Example 3).

EXAMPLE 3

Purification of the Anti-pl.GPx Antibodies by Affinity Chromatography

In order to selectively recover antibodies specific for pl.GPx, the sera recovered (Example 2) were subjected to a purification by affinity chromatography on a gel grafted with the oligopeptide which served as immunogen, according to the following procedure:

*Grafting of 10 mg of peptide onto 1 ml of high-performance SEPHAROSE gel (PHARMACIA®) pre-activated by means of N-hydroxysuccinimide (NHS-activated HiTrap column). Deactivation of the active groups not coupled to the ligand and washing of the non-specifically bound ligands using a 0.5M saline solution of ethanolamine pH 8.3 and a 0.1M saline solution of acetate pH 4.0. These solutions both contain 0.5M NaCl and are used alternately over cycles of 6 ml of each solution at each step (three cycles). Then equilibrate the column with a PBS solution before loading the serum.

*Loading of about 10 ml of rabbit serum onto the column previously equilibrated with PBS buffer (phosphate-buffered saline).

*Washing the column with PBS buffer.

*Elution of the specific anti-peptide antibodies by passing 0.1M citrate buffer pH 2.

*Concentration of the antibodies on ultrafiltration membrane (10 to 30,000 cut-off).

The antibodies thus purified specifically recognize human pl.GPx and no significant cross reaction is observed with human c.GPx. These antibodies are capable of recognizing the human pl.GPx bound to an insoluble support or in solution in a licuid phase.

EXAMPLE 4

Titration of an Antibody Solution

The titration method can be applied to sera collected during the selection of the peptides as well as to the specific antibody purified, according to Example 3. The method is based on the recognition of antigen insolubilized on a microtitre plate and the revealing of the antibody bound by a labelled anti-antibody. 96-well microplates, conventionally used for titrations in various fields, are preferably used. The titration is carried out according to the following procedure:

*Sensitize the wells of the microplate with 100 µl of antigen solution (oligopeptide or purified naturally occurring pl.GPx) at 2 or 1 µg/ml respectively (sensitization buffer: 10 mM Tris-HCl, pH 8.5, 100 mM NaCl).

*Cover the plate with a self-adhesive sheet and then incubate it overnight at 4° C. or for 2 hours at 37° C.

*Empty the wells and saturate the non-specific binding sites with a solution of protein such as for example 0.5% gelatine prepared with 50 mM Tris-HCl buffer, pH 7.8, 150 mM NaCl for 30 minutes at room temperature.

*Empty then wash the wells 3 times with 50 mM Tris-HCl solution at pH 7.8 containing 150 mM NaCl and 0.1% TWEEN 20.

*After removal of the last washing solution, distribute 100 µl of dilution buffer (50 mM Tris-HCl buffer at pH 7.8 containing 150 mM NaCl, 0.1% TWEEN 20 and 0.5% gelatine) into all the wells except the first well of each line. Each of the unused wells is reserved for the deposition of each of the samples (serum or purified antibody) to be tested and of the control serum (negative control). These samples should often be diluted 50 to 200 fold with the dilution buffer. The volume of deposit is 200 µl in all cases. The dilutions (2-fold serial dilution) are performed from well to well by transferring 100 µl of solution. The transfer starts with the well containing the 200 µl of serum sample to be tested. Make provisions to reserve at least one well for the internal zero of the test, which is performed at the time of the optical density readings: this well should not be used to dilute any serum and should therefore contain only the dilution buffer. The 100 µl removed from the last well are eliminated.

*Cover the plate with a self-adhesive sheet and then incubate for 2 hours at room temperature.

*Empty the plate and wash the wells with a series of 5 successive washes.

*Eliminate the last washing solution and then distribute 100 µl of revealing solution, that is to say an anti-antibody conjugate labelled (for example with alkaline phosphatase). This anti-antibody is specific for the species from which the serum is obtained (rabbit, mouse, goat, and the like). The solution of conjugate is diluted with the dilution buffer (50 mM Tris-HCl buffer pH 7.8 containing 150 mM NaCl, 0.1% TWEEN® 20 and 0.5% gelatine).

*Cover the plate with a self-adhesive sheet and then leave to incubate for 1 hour at room temperature.

*Empty the plate and wash the wells with a series of 5 successive washes.

*Distribute 100 µl of a solution of substrate, such as for example para-nitrophenyl phosphate in the case where alkaline phosphatase is used as revealing enzyme. The pNPP is prepared in an amount of 1 mg/ml of reagent in 0.1M Tris-HCl buffer pH 9.5 containing 1.35M NaCl.

*Incubate the plate at 37° C. after having covered it with a self-adhesive sheet. The optical density of each of the wells is read at 405 nm after about 20 minutes. After recording the signals obtained, the optical density values are represented by means of a graph as a function of the logarithm of the serum dilution. The titre value is set as being equal to the dilution value for which 50% of the antigen-antibody complex are obtained.

EXAMPLE 5

Evaluation of the Competition Between Insolubilized pl.GPx and pl.GPx in Solution for the Binding of the Specific Antibodies As mentioned in Example 1, the anti-peptide antibody was also chosen for its capacity to bind pl.GPx in solution. This capacity is essential for its use in an immunocapture assay test, which is the aim of the present invention. In order to evaluate this capacity, a competition test between pl.GPx in solution and pl.GPx adsorbed onto the microtitre plate is performed according to the following procedure:

a—The day before the assay itself:

*Sensitize the plate with pl.GPx at 1 µg/ml in 10 mM Tris-HCl buffer pH 8.5 containing 100 mM NaCl.
 *Cover the plate by means of a self-adhesive sheet and then leave to incubate overnight at 4° C.
 *Preparation of the solutions containing the pl.GPx/anti-peptide mixture.

Preliminary remarks:

The quantity of antibody to be introduced is constant and is not set at random. The final dilution of the concentrated solution of antibodies purified by affinity is determined after its titration (cf. preceding procedure): it is the dilution for which an optical density equal to 1 unit is arbitrarily obtained after 30 minutes incubation at 37° C.

The diluent for the antibodies and the free antigen (pl.GPx) consists of 50 mM Tris-HCl buffer pH 7.8 containing 150 mM NaCl, 0.1% TWEEN® 20 and 0.1% casein.

The inhibitor concentration may vary between 20 µg/ml and 7.5 ng/ml. The test described below uses concentrations of between 20 and 0.040 µg/ml.

Distribute 100 µl of diluent in test tubes numbered from 2 to 10 and intended for the preparation of the series for the antibody—competitor mixture (pl.GPx in solution). Introduce 200 µl of pl.GPx solution at 40 µg/ml in tube no. 1. Transfer 100 µl of the solution contained in tube no. 1 into tube no. 2, then from tube no. 2 to tube no. 3 and so on for the next tubes. The 100 µl collected from the last tube are eliminated. Prepare the antibody solution at a concentration double the final concentration expected in the microplate well, then distribute into all the tubes 100 µl of the antibody solution and leave the mixtures to incubate overnight at 4° C.

b—On the day of the test.

*Empty the wells of the microplate.
 *Saturate the non-specific binding sites by means of a protein solution at 0.2%–1% (gelatine, ovalbumin, bovine serum albumin)
 *Deposit 100 µl of each series point from tube no. 1 to tube no. 10 into a distinct well.
 *Leave to incubate for 2 hours at room temperature.
 *Empty the wells and perform 5 successive washes.
 *Eliminate the last washing solution and then distribute 100 µl of the solution of anti-antibody conjugate labelled (for example with alkaline phosphatase). This anti-antibody is specific for the species from which the serum is obtained (rabbit, mouse, goat and the like). The solution of conjugate is diluted with the dilution buffer (50 mM Tris-HCl buffer pH 7.8 containing 150 mM NaCl, 0.1% TWEEN® 20 and 0.5% gelatine).
 *Cover the plate with a self-adhesive sheet and then leave to incubate for 1 hour at room temperature.
 *Empty the plate and wash the wells with a series of 5 successive washes.
 *Distribute 100 µl of a solution of substrate, such as for example para-nitrophenyl phosphate in the case where alkaline phoephatase is used as revealing enzyme. The pNPP is prepared in an amount of 1 mg/ml of reagent in a 0.1M Tris-HCl buffer pH 9.5 containing 1.35M NaCl. Incubate the plate at 37° C. after having covered it with a self-adhesive sheet. The optical density of each of the wells is read at 405 nm after about 30 minutes. Let B be the signal obtained in the presence of inhibitor, $B_o$ be the signal obtained in the absence of inhibitor and $b_f$ the signal corresponding to the background noise (absence of antibody and of free pl.GPx). The weaker the inhibition, the stronger the intensity of the signal read (B). The graphical representation of B-bf/Bo-bf as a function of the log. of the free pl.GPx concentration makes it possible to visualize the influence of the increasing concentration of free pl.GPx on the recognition of the pl.GPx bound to the plate by the specific anti-peptide antibodies and makes it possible to calculate the concentration of pl.GPx necessary to give a 50% inhibition of the binding of the antibody to the pl.GPx adsorbed.

EXAMPLE 6

Development of an Immunoassay Method Specific for pl.GPx

The anti-peptide antibodies purified as described in Example 3 were used to perform an immunoenzymatic assay of the extraction-saturation or "sandwich" type in which—the anti-peptide antibodies are absorbed in the wells of the microplate (they are the "capturing" antibodies)—the pl.GPx present in the sample to be assayed is "immunocaptured" by the antibodies adsorbed —the presence of pl.GPx is revealed by a second "tracer" antibody labelled with an enzyme.

The assay was carried out according to the following procedure:

The anti-pl.GPx antibodies used as tracer antibodies are obtained from sera collected from rabbits immunized against the naturally occurring protein purified from human plasmas.

These anti-pl.GPx antibodies are purified by double-extraction with caproic acid, then with ammonium sulphate. They are then labelled with biotin.

The anti-peptide antibodies (Example 3) are bound to an insoluble support which may be microtitre plate wells, polystyrene beads or any other material capable of adsorbing antibodies. A 96-well microplate is used for example. The plate is sensitized with 200 µl of an antibody solution at 2–10 µg/ml. These antibodies are in saline solution (Tris, phosphate, carbonate buffer) at pH 7–9. The incubation lasts for two hours at 37° C. or overnight at 4° C. After sensitization, the plate is washed, then the non-specific binding sites are saturated by means of either a solution of sugars, or a solution of protein such as casein, gelatine, BSA or ovalbumin. This step lasts for about 30 minutes to two hours at 37° C.

The plate is washed, then the sample to be assayed is deposited in an amount of 100 μl of solution per well. The plate is incubated for one to two hours at 37° C. The wells are then emptied and then washed with the washing buffer.

A volume of 100 μl of solution of anti-pl.GPx antibody is deposited in each well. The whole is incubated for two hours at 37° C.

The plate is again washed and then 100 μl of solution of alkaline phosphatase-labelled avidin are deposited into each well. The incubation at 37° C. is then maintained for one hour. The wells are emptied, washed and then emptied before introducing 100 μl of a pNPP solution.

The optical densities of the solutions contained in each of the wells are read at 405 nm with a 96-well microtitre plate reader. A volume of 50 μl of stop solution (1M sodium hydroxide) is added when the highest optical density reaches 2 to 2.5 units, that is to say after 20 to 30 minutes of incubation at 37° C.

The following table makes it possible to establish a standard curve by plotting the O.D. measured as a function of the logarithm of the pl.GPx concentration.

| pl.GPx concentration | | |
| --- | --- | --- |
| ng/ml | log | Optical Density |
| 600 | 2.78 | 2.47 |
| 300 | 2.48 | 1.97 |
| 150 | 2.18 | 1.32 |
| 75 | 1.88 | 0.77 |
| 37.5 | 1.57 | 0.43 |
| 18.8 | 1.27 | 0.22 |
| 9.4 | 0.97 | 0.10 |

The biological samples to be assayed are measured in the same manner and evaluated relative to the standard curve.

If the spectrophotometric microplate reader comprises a suitable software for calculation, the representation can be made directly by the latter.

EXAMPLE 7

The method developed in the preceding example served as the basis for the development of a ready-for-use kit for assaying pl.GPx in any dissolved blood or tissue sample. This kit comprises all the following constituents:

1—96-well immunotitre plate sensitized with the purified anti-peptide antibody. It can be a divisible plate (strips of 8, 16, 24 or 48 wells) or a non-divisible plate. In all cases, the strips or the plate are packaged in a blister in the presence of a dessicating agent for their preservation.

2—Solution for diluting the samples: buffered solution (Tris, phosphate) containing a protein (such as casein, BSA, ovalbumin) at a concentration of the order of 0.1% to 1%, an ionic or non-ionic detergent and a preserving agent (sodium azide or merthiolate).

3—Freeze-dried standard: this is human pl.GPx purified from human plasmas and freeze-dried.

4—Concentrated washing buffer: buffered solution (Tris, phosphate) containing NaCl, a detergent and a preserving agent such as those described above.

5—Solution of labelled tracer antibodies: this may be an anti-human pl.GPx monoclonal or polyclonal antibody obtained by immunization of animals with purified human pl.GPx. These antibodies are labelled with biotin or coupled to a revealing enzyme (alkaline phosphatase or PAL, horseradish peroxidase or HRP). These antibodies are in solution in a mixture containing Tris or phosphate buffer, NaCl (150 mM), an overload protein (BSA, OVA, casein) at 0.1–1%, glycerol and a preserving agent.

6—A solution of avidin coupled to a revealing enzyme: this solution is present only when the tracer antibody is biotinylated. Either avidin or streptavidin may be used. This protein may be coupled to PAL or HRP. It is in saline solution (Tris, phosphate) with an overload protein (BSA, OVA, casein) and a preserving agent adapted to the type of revealing (sodium azide proscribed for peroxidase).

7—Revealing substrate(s): pNPP in the case of alkaline phosphatase and ortho-phenylenediamine (OPD) in the case of peroxidase.

8—Substrate dilution buffer:

Basic buffer (Tris, ethanolamine) pH 9.5 containing magnesium chloride and a preserving agent (sodium azide or merthiolate) in the case of alkaline phosphatase.

Acidic buffer (for example citrate pH 5.5) containing hydrogen peroxide (about 0.012%) and a preserving agent (merthiolate) in the case of peroxidase.

9—Stop solution:

*1M sodium hydroxide solution containing a metal chelator such as 0.1M ethylenediaminetetraacetate (EDTA) in the case of alkaline phosphatase;

*1M sulphuric acid solution in the case of revealing with peroxidase.

The implementation of the test is performed according to the following procedure:

Collect venous blood in a glass tube without anticoagulant. Leave the blood to stand for a minimum of two hours before removing the serum. Centrifuge for 10 minutes at 2000×g and recover the serum. The serum samples are stable for 24 hours at 4° C. Beyond that, it is advisable to freeze the samples at −20° C., or better at −80° C.

Dilution: the serum samples should be diluted in the solution for diluting the samples. A dilution value of between 1:40 and 1:80 is generally sufficient.

Follow the procedure described in Example 6.

The sensitivity of the test is excellent: from 36 simultaneous measurements of the blank (sample diluent) carried out on the same day and on the same plate, the detection limit determined is less than 10 ng/ml.

We claim:

1. A synthetic oligopeptide having an amino acid sequence consisting of Glu Pro Gly Glu Asn Ser Glu Ile Leu Pro Thr Leu Lys (residues 108–120 of SEQ ID No. 1); or variant thereof, wherein the variant is a one or two amino acid substitution of the oligopeptide with an equivalent amino acid or the variant is a single amino acid addition on the C-terminal end of the oligopeptide or the variant is a single tyrosine addition on the N-terminal end of the oligopeptide; and wherein antibodies raised against the oligopeptide or the variant are specific for plasma glutathione peroxidase (pl.GPx) and distinguish between said pl.GPx and intracellular glutathione peroxidase (c.GPx).

2. A synthetic oligopeptide having an amino acid sequence consisting of Glu Pro Gly Glu Asn Ser Glu Ile Leu Pro Thr Leu Lys (residues 108–120 of SEQ ID No. 1).

3. A synthetic oligopeptide having an amino acid sequence consisting of Glu Pro Gly Glu Asn Ser Glu Ile Leu Pro Thr Leu Lys Tyr (residues 108–121 of SEQ ID No 1).

4. An immunogenic conjugate comprising: a carrier protein and a synthetic oligopeptide having an amino acid sequence consisting of Glu Pro Gly Glu Asn Ser Glu Ile Leu Pro Thr Leu Lys (residues 108–120 of SEQ ID No. 1); or variant thereof, wherein the variant is a one or two amino acid substitution of the oligopeptide with an equivalent amino acid or the variant is a single amino acid addition on at least one N-terminal or C-terminal end of the oligopeptide and wherein antibodies raised against the oligopeptide or the variant are specific for plasma glutathione peroxidase (pl.GPx) and distinguish between said pl.GPx and intracellular glutathione peroxidase (c.GPx).

5. The immunogenic conjugate of claim 4, wherein the variant has tyrosine grafted on at least one N-terminal or C-terminal end of the oligopeptide (residues 108–120 of SEQ ID No. 1).

6. The immunogenic conjugate of claim 4, wherein the carrier protein is selected from the group consisting of ovalbumin, bovine serum albumin, keyhole limpet hemocyanin.

7. The immunogenic conjugate of claim 6, wherein the carrier protein is bovine serum albumin.

8. The immunogenic conjugate of claim 4, wherein the variant is a single tyrosine addition at the N-terminal end.

9. An immunogenic conjugate comprising an oligopeptide having an amino acid sequence consisting of Glu Pro Gly Glu Asn Ser Glu Ile Leu Pro Thr Leu Lys (residues 108–120 of SEQ ID No. 1) and a carrier protein.

10. An immunogenic conjugate comprising an oligopeptide having an amino acid sequence consisting of Glu Pro Gly Glu Asn Ser Glu Ile Leu Pro Thr Leu Lys Tyr (residues 108–121 of SEQ ID No. 1) and a carrier protein.

11. Antibodies raised against an immunogenic conjugate comprising a synthetic oligopeptide or variant thereof coupled to a carrier protein wherein the oligopeptide has an amino acid sequence consisting of Glu Pro Gly Glu Asn Ser Glu Ile Leu Pro Thr Leu Lys (residues 108–120 of SEQ ID No. 1); wherein the variant is a one or two amino acid substitution of the oligopeptide with an equivalent amino acid or the variant is a single amino acid addition on at least one N-terminal or C-terminal end of the oligopeptide and wherein said antibodies bind epitopes having the amino acid sequence Glu Pro Gly Glu Asn Ser Glu Ile Leu Pro Thr Leu Lys (residues 108–120 of SEQ ID No. 1), are specific for plasma glutathione peroxidase (pl.GPx) and distinguish between said pl.GPx and intracellular glutathione peroxidase (c.GPx).

12. The antibodies of claim 11, wherein the variant has tyrosine grafted on at least one of the N-terminal and the C-terminal ends of the oligopeptide (residues 108–120 of SEQ ID No. 1).

13. The antibodies of claim 11, wherein the variant has an amino acid sequence consisting of Glu Pro Gly Glu Asn Ser Glu Ile Leu Pro Thr Leu Lys Tyr (residues 108–121 of SEQ ID No. 1).

14. The antibodies of claim 11, wherein the carrier protein is selected from the group consisting of ovalbumin, bovine serum albumin, keyhole limpet hemocyanin.

15. The antibodies of claim 14, wherein the carrier protein is bovine serum albumin.

16. The antibodies of claim 11, wherein the variant is a single tyrosine addition at the N-terminal end.

17. A method for producing antibodies comprising:
injecting into animals an immunogenic conjugate comprising a synthetic oligopeptide or variant thereof coupled to a carrier protein wherein the oligopeptide has an amino acid sequence consisting of: Glu Pro Gly Glu Asn Ser Glu Ile Leu Pro Thr Leu Lys (residues 108–120 of SEQ ID No. 1); wherein the variant is a one or two amino acid substitution of the oligopeptide with an equivalent amino acid or the variant is a single amino acid addition on at least one N-terminal or C-terminal end of the oligopeptide; and
collecting the antibodies produced, said antibodies being specific for plasma glutathione peroxidase (pl.GPx) and distinguish between said pl.GPx and intracellular glutathione peroxidase (c.GPx).

18. The method of claim 17, wherein the variant is a single tyrosine addition at the N-terminal end.

19. The method of claim 17, wherein the variant has tyrosine grafted on at least one of the N-terminal and the C-terminal ends of the oligopeptide (residues 108–120 of SEQ ID No. 1).

20. The method of claim 17, wherein the variant has an amino acid sequence consisting of Glu Pro Gly Glu Asn Ser Glu Ile Leu Pro Thr Leu Lys Tyr (residues 108–121 of SEQ ID No. 1).

21. A method of producing antibodies comprising:
injecting into animals an immunogenic conjugate comprising a synthetic oligopeptide having an amino acid sequence consisting of Glu Pro Gly Glu Asn Ser Glu Ile Leu Pro Thr Leu Lys (residues 108–120 of SEQ ID No. 1) and a carrier protein; and
collecting the antibodies produced.

22. A method for determining plasma glutathione peroxidase (pl.GPx) in a biological sample comprising the following steps:
providing antibodies specific for said pl.GPx, which distinguish between said pl.GPx and intracellular glutathione peroxidase (c.GPx), bound to a support;
contacting the antibodies specific for the pl.GPx with the biological sample so that the antibodies immunocapture any pl.GPx present in the sample; and
detecting said immunocaptured pl.GPx, and therefore detecting any said pl.GPx in the biological sample, by contacting with labeled pl.GPx antibodies so that the labeled pl.GPx antibodies bind the immunocaptured pl.GPx, wherein the antibodies specific for said pl.GPx and bound to the support are raised against an immunogenic conjugate comprising a synthetic oligopeptide or variant thereof coupled to a carrier protein, wherein the oligopeptide has an amino acid sequence consisting of:
Glu Pro Gly Glu Asn Ser Glu Ile Leu Pro Thr Leu Lys (residues 108–120 of SEQ ID NO. 1); and the variant is a one or two amino acid substitution of the oligopeptide with an equivalent amino acid or the variant is a single amino acid addition on at least one N-terminal or C-terminal end of the oligopeptide.

23. The method of claim 22, wherein the labeled pl.GPx antibodies are antibodies raised against purified pl.GPx in an animal or a human.

24. The method of claim 22 further comprising quantifying the pl.GPx detected in the biological sample by comparing with a standard reference curve obtained using a purified sample of pl.GPx.

25. The method of claim 22, wherein the variant has tyrosine grafted on at least one of the N-terminal and the C-terminal ends of the oligopeptide (residues 108–120 of SEQ ID No. 1).

26. The method of claim 22, wherein the variant has an amino acid sequence consisting of Glu Pro Gly Glu Asn Ser Glu Ile Leu Pro Thr Leu Lys Tyr (residues 108–121 of SEQ ID No. 1).

27. A kit for assaying plasma glutathione peroxidase (pl.GPx) comprising:
- micro titer plates having wells coated with antibodies specific for said pl.GPx and which distinguish between said pl.GPx and intracellular glutathione peroxidase (c.GPx), wherein the antibodies are raised against an immunogenic conjugate comprising a synthetic oligopeptide or variant thereof coupled to a carrier protein wherein the oligopeptide has an amino acid sequence consisting of:
- Glu Pro Gly Glu Asn Ser Glu Ile Leu Pro Thr Leu Lys (residues 108–120 of SEQ ID No 1); wherein the variant is a one or two amino acid substitution of the oligopeptide with an equivalent amino acid or the variant is a single amino acid addition on at least one N-terminal or C-terminal end of the oligopeptide,
- solutions of diluent and washing buffer,
- a freeze-dried pl.GPx standard, and
- a solution of labeled pl.GPx antibodies.

28. The kit of claim 27, wherein the labeled pl.GPx antibodies are antibodies raised against purified pl.GPx in an animal or human.

29. The kit of claim 27, wherein the variant has tyrosine grafted on at least one of the N-terminal and the C-terminal ends of the oligopeptide (residues 108–120 of SEQ ID No. 1).

30. The kit of claim 27, wherein the variant has an amino acid sequence consisting of Glu Pro Gly Glu Asn Ser Glu Ile Leu Pro Thr Leu Lys Tyr (residues 108–121 of SEQ ID No. 1).

31. The kit of claim 27, wherein the variant has tyrosine grafted on the N-terminal end of the oligopeptide (residues 108–120 of SEQ ID No. 1).

32. The method of claim 22, wherein the variant has tyrosine grafted on the N-terminal end of the oligopeptide (residues 108–120 of SEQ ID No. 1).

* * * * *

SEQUENCE LISTING ( 1 ) GENERAL INFORMATION:

( i i i ) NUMBER OF SEQUENCES: 1

(2) INFORMATION FOR SEQ ID NO:1:

(i) SEQUENCE CHARACTERISTICS:
    (A) LENGTH: 226 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (ix) FEATURE:
    (A) NAME/KEY: Modified-site
    (B) LOCATION: 73
    (D) OTHER INFORMATION: /note= "Amino acid at position 73 is selenocysteine"

(xi) SEQUENCE DESCRIPTION: SEQ ID NO:1:

```
Met Ala Arg Leu Leu Gln Ala Ser Cys Leu Leu Ser Leu Leu Leu Ala
 1               5                  10                  15
Gly Phe Val Ser Gln Ser Arg Gly Gln Gly Lys Ser Lys Met Asp Cys
             20                  25                  30
His Gly Gly Ile Ser Gly Thr Ile Tyr Glu Tyr Gly Ala Leu Thr Ile
         35                  40                  45
Asp Gly Glu Glu Tyr Ile Pro Phe Leu Gln Tyr Ala Gly Lys Tyr Val
     50                  55                  60
Leu Phe Val Asn Val Ala Ser Tyr Xaa Gly Leu Thr Gly Gln Tyr Ile
 65                  70                  75                  80
Gly Leu Asn Ala Leu Gln Glu Glu Leu Ala Pro Phe Gly Leu Val Ile
             85                  90                  95
Leu Gly Phe Pro Cys Asn Gln Phe Gly Lys Gln Glu Pro Gly Glu Asn
            100                 105                 110
Ser Glu Ile Leu Pro Thr Leu Lys Tyr Val Arg Pro Gly Gly Gly Phe
            115                 120                 125
Val Pro Asn Phe Gln Leu Phe Glu Lys Gly Asp Val Asn Gly Glu Lys
    130                 135                 140
Glu Gln Lys Phe Tyr Thr Phe Leu Lys Asn Ser Cys Pro Pro Thr Ser
145                 150                 155                 160
Glu Leu Leu Gly Thr Ser Asp Arg Leu Phe Trp Glu Pro Met Lys Val
                165                 170                 175
His Asp Ile Arg Trp Asn Phe Glu Lys Phe Leu Val Gly Pro Asp Gly
            180                 185                 190
Ile Pro Ile Met Arg Trp His His Arg Thr Thr Val Ser Asn Val Lys
        195                 200                 205
Met Asp Ile Leu Ser Tyr Met Arg Arg Gln Ala Ala Leu Gly Val Lys
    210                 215                 220
Arg Lys
225
```